United States Patent [19]

Soyama et al.

[11] Patent Number: 5,071,639

[45] Date of Patent: Dec. 10, 1991

[54] NAIL COSMETIC COMPOSITION

[75] Inventors: Yoshikazu Soyama; Makoto Takahashi; Yoshiyuki Ogusu; Toru Okamoto; Motokiyo Nakano, all of Yokohama, Japan

[73] Assignee: Shiseido Company Ltd., Tokyo, Japan

[21] Appl. No.: 427,134

[22] PCT Filed: Mar. 22, 1989

[86] PCT No.: PCT/JP89/00301

§ 371 Date: Oct. 20, 1989

§ 102(e) Date: Oct. 20, 1989

[30] Foreign Application Priority Data

Mar. 22, 1988 [JP] Japan .................................. 63-67966
Aug. 9, 1988 [JP] Japan .................................. 63-197063

[51] Int. Cl.$^5$ ........................................... N61K 7/043
[52] U.S. Cl. .......................................... 424/61; 106/3
[58] Field of Search .............................. 424/61; 106/3

[56] References Cited

U.S. PATENT DOCUMENTS

| | | | |
|---|---|---|---|
| 4,222,908 | 9/1980 | Ikeda et al. | 424/61 X |
| 4,229,227 | 10/1980 | Ikeda et al. | 424/61 X |
| 4,822,423 | 4/1989 | Soyama et al. | 424/61 X |

FOREIGN PATENT DOCUMENTS

| | | | |
|---|---|---|---|
| 2913344 | 10/1979 | Fed. Rep. of Germany | 424/61 |
| 2568471 | 2/1986 | France | 424/61 |
| 58-144312 | 8/1983 | Japan | 424/61 |
| 60-16910 | 1/1985 | Japan | 424/61 |
| 2021411 | 12/1979 | United Kingdom . | |

Primary Examiner—Thurman K. Page
Assistant Examiner—Susan S. Rucker
Attorney, Agent, or Firm—Sprung Horn Kramer & Woods

[57] ABSTRACT

A nail cosmetic composition containing an organically modified montmorillonite, a silica and a nonaromatic solvent, and preferably an anionic surfactant, is safe for use on the human body and is free from sedimentation of a pearl agent contained therein, has an excellent stability over a long period, and has good physical properties such as coating and useability.

8 Claims, No Drawings

NAIL COSMETIC COMPOSITION

TECHNICAL FIELD

The present invention relates to a novel nail cosmetic composition. More specifically, it relates to a nail cosmetic composition containing an organically modified montmorillonite, a silica and a nonaromatic solvent, and preferably, an anionic surfactant additionally formulated therein.

Namely, the present invention relates to a nail cosmetic composition which has no harmful affect on the human body, is free from any sedimentation of the pigment or pearl agent contained therein, has an excellent stability over a long period, and has good physical properties such as coating and useability.

BACKGROUND ART

In the prior art, an organically modified montmorillonite is formulated in a nail cosmetic composition and sedimentation of the pigment or pearl agent therein is prevented by utilizing the good thixotropy imparting property of this clay mineral, and in this case, an aromatic solvent such as toluene, xylene or the like is used as the solvent. An aromatic hydrocarbon solvent such as toluene can provide the most desirable gel by causing the clay to swell, and a nail cosmetic composition containing such a gel exhibits a relatively good dispersion stability without sedimentation or separation over a long period, and thus it is considered that toluene, etc. must be used as the solvent for this kind of nail cosmetic composition. Also, it is known that the dispersion stability and stability over a long period can be further improved by formulating a hydrophobic silica (see Japanese Unexamined Patent Publication (Kokai) No. 62-174003), but since gel compositions in which toluene is essential are employed, the nail cosmetic composition necessarily contains toluene. On the other hand, as a gel composition for a nail cosmetic composition not containing an aromatic hydrocarbon solvent such as toluene or xylene, etc., a composition is known which comprises a hydroxyl containing a polar substance and a phenyl containing an organic silicone compound specifically formulated therein (see Japanese Patent Publication (kokoku) no. 61-001044), whereby a method by which a nail cosmetic composition is made safe for use on the human body is established.

An aromatic hydrocarbon solvent such as toluene, xylene or the like is known to cause problems with regard to the safe use thereof on the human body, particularly there is a danger of damage to the nails or a feeling of pain arising when the cosmetic nail composition is used frequently. Also, the nail cosmetic composition not containing an aromatic hydrocarbon solvent such as toluene, xylene, or the like as disclosed in Japanese Patent Publication (Kokoku) No. 61-001044, which although safe for use on the human body, imparts a thixotropic property, and has a relatively good dispersion stability and stability over a long period, is not fully satisfactory from the aspect of stability.

DISCLOSURE OF THE INVENTION

Accordingly, in view of the state of the art as described above, an object of the present invention is to develop a nail cosmetic composition which is safe for use on the human body, has an excellent dispersion stability and safety over a long period, and has excellent physical properties such as coating and useability.

Other objects of the present invention, and the advantages obtained according to the present invention, will be apparent from the following description.

According to the present invention, there is provided a nail cosmetic composition, which is safe for use on the human body, free from sedimentation of a pigment or pearl agent contained therein, has an excellent stability over a long period, and has excellent physical properties such as coating and useability, comprising an organically modified montmorillonite, a silica, and a nonaromatic solvent as essential ingredients.

Also, according to the present invention, a further improved nail cosmetic composition having a prolonged stability and comprising an organically modified montmorillonite, a silica, an anionic surfactant, and a nonaromatic solvent as essential ingredients, is provided.

EMBODIMENTS FOR CARRYING OUT THE INVENTION

Aromatic hydrocarbon solvents such as toluene, xylene, or the like and a phenyl group containing organic silicones, etc., as used in the prior art, are substances which cause clay to swell and impart a thixotropic property thereto. The present invention, however, imparts an excellent thixotropic property to the nail cosmetic composition through a mutual interaction between the organically modified montmorillonite and the silica, by using a nonaromatic solvent safe for use on the human body and not using toluene, xylene, or the like, and further, has an improved and prolonged stability when an anionic surfactant is formulated therein.

The organically modified montmorillonite to be used in the present invention is a substance having a quaternary ammonium type cationic surfactant, or a nonionic higher oranic polar compound chemically bound to montmorillonite, which is a clay mineral including, for example, Benton (Benton 27, Benton 34, Benton 38, manufacture by National Red) as commercially available products, any one of which can be utilized and selected as desired, and further one or two or more kinds thereof can be formulated. Preferably, the amount formulated of these components is 0.2 to 3.0% by weight, more preferably 0.8 to 2.0% by weight. When the amount formulated is less than 0.2% by weight, it is difficult to obtain a good thixotropic property, and conversely, when this amount exceeds 3.0% by weight, the coating gloss and durability (peeling) over a long period of the nail cosmetic composition become poor.

The silica to be used in the present invention may be well known in the art, and may include hydrophilic silicas such as Aerosil #200, Aerosil #300, Aerosil #380, or hydrophobic silicas such as Aerosil R972, as commercially available products. Among the above, those having a particle size of less than 0.01 μm, such as Aerosil #200, Aerosil #300, Aerosil #380, are preferable from the viewpoint of the thixotropic property thereof.

Preferably, the amount formulated of these components is 0.1 to 2.0% by weight, more preferably 0.5 to 1.5% by weight. When the amount formulated is less than 0.1% by weight, it is difficult to obtain a good thixotropic property and the stability over a long period may become poor. Conversely, when this amount exceeds 2.0% by weight, the gloss of the enamel coating becomes poor during use, and the durability (peeling) over a long period also becomes poor.

The anionic surfactant to be used in the preferred embodiment of the present invention may be any known in the art including, for example, sulfosuccinates such as sodium dioctylsulfosuccinate, calcium dioctylsulfosuccinate, barium dioctyl-sulfosuccinate, sodium di-2-ethylhexylsulfosuccinate, sodium di-n-hexylsulfosuccinate and the like; N-acylsarcosinates such as sodium lauroylsarcosinate, calcium lauroylsarcosinate, sodium palmitoylsarcosinate and the like; alkyl sulfate salts such as sodium lauryl sulfate, calcium lauryl sulfate, sodium myristyl sulfate, sodium cetyl sulfate and the like; polyoxyethylene (hereinafter abbreviated as "POE") alkyl ether sulfate salts such as sodium POE lauryl ether sulfate, triethanolamine POE lauryl ether sulfate, and triethanolamine POE nonyl phenyl ether sulfate, etc.

Preferably, the amount formulated of the anionic surfactant is 0.01 to 1.5% by weight, more preferably 0.1 to 1.0% by weight. When the amount formulated is less than 0.01% by weight, the prolongation of the stability is not always satisfactory, and conversely, when this amount exceeds 1.5% by weight, the durability (peeling) over a long period becomes poor.

The nonaromatic solvent to be used in the present invention refers broadly to organic solvents other than aromatic solvents such as toluene, xylene, or the like and includes, for example, n-butyl acetate, isobutyl acetate, ethyl acetate, methyl ethyl ketone, acetone, n-butanol, isopropyl alcohol, and ethyl alcohol, etc. Either one or two or more kinds of these solvents can be formulated. Preferably, the amount formulated of these components is 60 to 85% by weight.

Further, in addition to the above essential components, general purpose additives conventionally used in nail cosmetic compositions, such as film forming agents, resins, plasticizers, pigments, and pearl agents, can be formulated in the nail cosmetic composition of the present invention, and UV-ray absorbers, humectants, drugs, perfumes, and water can be also added in appropriate amounts, as long as they are used under the qualitative and quantitative conditions which do not impair the object of the present invention.

The present invention concerns a nail cosmetic composition safe for use on the human body, having an excellent stability over a long period without sedimentation of the pigment or pearl agent contained therein and good physical properties such as coating and useability. Compared with prior art compositions using an aromatic hydrocarbon solvent such as toluene, xylene, or the like, the safety when used on the human body is high, in that little damage or pain are caused, and the durability (peeling) over a long period is excellent. Also, compared with nail cosmetic compositions not containing an aromatic hydrocarbon solvent such as toluene, xylene, or the like, the qualities thereof with respect to sedimentation of the pearl agent, stability over a long period, and physical properties such as coating and useability are also excellent.

EXAMPLES

The present invention is described in more detail with reference to Examples, which in no way limit the scope of the present invention. Prior to the Examples, the effect testing methods and evaluation methods are described in detail.

Viscosity

Measured by BL-type viscometer rotor No. 2 for one minute at 6 rpm and 30° C.

Stability with Elapse of Time

The nail cosmetic composition is filled in a vessel, and the sedimentation and separation over a long period (at 50° C. for 2 months) are observed with the naked eye.

⊚: no sedimentation or separation
○: slight sedimentation or separation
▲: sedimentation or separation observed
△: much sedimentation or separation observed

Gloss of Coating

Evaluated organoleptically during actual use.

⊚: very glossy
○: slightly glossy
◉: slight loss of gloss
△: very little gloss
X : no gloss

Durability with Elapse of Time

Evaluated organoleptically during actual use (3 days).

⊚: very good durability
○: good durability
◉: not very good durability
△: poor durability
X: very poor durability

Safety When Used on Human Body (Nail Abnormalities)

Evaluated organoleptically during actual use.
n=50

⊚: nail abnormalities observed <3
○: nail abnormalities observed 3-5
◉: nail abnormalities observed 6-10
△: nail abnormalities observes 11-15
X : nail abnormalities observed ≧16

EXAMPLES 1 AND 2, COMPARATIVE EXAMPLE 1

According to the compositions shown in Table 1, nail cosmetic compositions were prepared in a conventional manner and the quality of the respective compositions was evaluated.

TABLE 1

|  | Comparative Example 1 | Example 1 | Example 2 |
|---|---|---|---|
| Nitrocellulose | 15.0 | 15.0 | 15.0 |
| Alkyd resin | 5.0 | 5.0 | 5.0 |
| Acrylic resin | 5.0 | 5.0 | 5.0 |
| Acetyltributyl citrate | 5.0 | 5.0 | 5.0 |
| Organic bentonite (Benton 27) | 1.0 | 1.0 | 1.0 |
| Isopropyl alcohol | 3.0 | 3.0 | 3.0 |
| Ethyl acetate | 10.0 | 10.0 | 10.0 |
| n-Butyl acetate | 32.0 | 50.0 | 50.0 |
| Butyl alcohol | 3.0 | 3.0 | 3.0 |
| Toluene | 18.0 | — | — |
| Pigment (Red color 202 1 Titanium dioxide 1) | 1.0 | 1.0 | 1.0 |
| Pearl agent | 1.0 | 1.0 | 1.0 |
| Aerosil R972*1 | 1.0 | — | 1.0 |
| Aerosil 380*2 | — | 1.0 | — |
| Viscosity cps | 1500 | 1500 | 800 |
| Stability with elapse | ⊚ | ⊚ | ⊚ |

TABLE 1-continued

|  | Comparative Example 1 | Example 1 | Example 2 |
|---|---|---|---|
| of time |  |  |  |
| Gloss of coating | ◉ | ◉ | ◉ |
| Durability (peeling) with elapse of time | ○ | ◉ | ◉ |
| Safety when used on human body | △ | ○ | ○ |

Aerosil R972*[1] particle size 0.016 μm
Aerosil 380*[2] particle size 0.007 μm

As apparent from the results shown in Table 1, Examples 1 and 2 are safe for use on the human body and have an excellent stability over a long period without sedimentation of the pigment or pearl agent contained therein, and have excellent physical properties such as coating and useability. In contrast, the nail cosmetic composition formulated with toluene and silica (Comparative Example 1), although having an excellent stability, has an inferior durability over a long period, safety when used on the human body, and produced nail abnormalities.

EXAMPLES 3-5

According to the compositions shown in Table 2, nail cosmetic compositions were prepared in a conventional manner and the quality of the respective compositions was evaluated.

TABLE 2

|  | Example 3 | Example 4 | Example 5 |
|---|---|---|---|
| Nitrocellulose | 15.0 | 15.0 | 15.0 |
| Alkyd resin | 5.0 | 5.0 | 5.0 |
| Acrylic resin | 5.0 | 5.0 | 5.0 |
| Acetyltriethyl citrate | 5.0 | 5.0 | 5.0 |
| Organic bentonite (Benton 38) | 0.2 | 3.0 | 1.0 |
| Isopropyl alcohol | 3.0 | 3.0 | 3.0 |
| Ethyl acetate | 15.0 | 15.0 | 15.0 |
| n-Butyl acetate | 44.8 | 43.9 | 43.0 |
| Butyl alcohol | 3.0 | 3.0 | 3.0 |
| Pigment (Red color 202 1 Titanium dioxide 1) | 1.0 | 1.0 | 1.0 |
| Pearl agent | 1.0 | 1.0 | 1.0 |
| Silica | 2.0 | 0.1 | 2.0 |
| particle size (μ) | (0.012) | (0.007) | (0.01) |
| Viscosity (cps) | 700 | 2000 | 1500 |
| Stability with elapse of time | ◉ | ◉ | ◉ |
| Gloss of coating | ◉ | ◉ | ◉ |
| Durability (peeling) with elapse of time | ◉ | ◉ | ◉ |
| Safety when used on human body | ○ | ○ | ○ |

As apparent from the results shown in Table 2, Examples 3 to 5 are safe for use on the human body and have an excellent stability with the elapse of time without sedimentation of the pigment or pearl agent contained therein, and have excellent physical properties such as coating and useability.

Examples 6 and 7, Comparative Example 2

According to the compositions shown in Table 3, nail cosmetic compositions were prepared in a conventional manner and the quality of the respective compositions was evaluated.

TABLE 3

|  | Comparative Example 2 | Example 6 | Example 7 |
|---|---|---|---|
| Nitrocellulose | 15.0 | 15.0 | 15.0 |
| Alkyd resin | 5.0 | 5.0 | 5.0 |
| Acrylic resin | 5.0 | 5.0 | 5.0 |
| Acetyltributyl citrate | 5.0 | 5.0 | 5.0 |
| Organic bentonite (Benton 27) | 1.0 | 1.0 | 1.0 |
| Isopropyl alcohol | 3.0 | 3.0 | 3.0 |
| Ethyl acetate | 10.0 | 10.0 | 10.0 |
| n-Butyl acetate | 30.0 | 47.5 | 47.5 |
| Butyl alcohol | 3.0 | 3.0 | 3.0 |
| Toluene | 18.0 | — | — |
| Pigment (Red color 202 1 Titanium dioxide 1) | 1.0 | 1.0 | 1.0 |
| Pearl agent | 3.0 | 3.0 | 3.0 |
| Aerosil R972*[1] | 1.0 | 1.0 | — |
| Aerosil 380*[2] | — | — | 1.0 |
| Barium dioctylsulfosuccinate | — | 0.5 | — |
| Sodium POE nonylphenyl ether sulfate | — | — | 0.5 |
| Viscosity (cps) | 1500 | 900 | 2000 |
| Stability with elapse of time | ○ | ◉ | ◉ |
| Gloss of coating | ◉ | ◉ | ◉ |
| Durability (peeling) with elapse of time | ○ | ◉ | ◉ |
| Safety when used on human body | △ | ○ | ○ |

Aerosil R972*[1] particle size 0.016 μm
Aerosil 380*[2] particle size 0.007 μm

As apparent from the results shown in Table 3, Examples 6 and 7, compared with Comparative Example 2, are safe for use on the human body and are free from sedimentation of the pigment or pearl agent contained therein, and have good physical properties such as coating and useability.

EXAMPLES 8 and 9

According to the compositions shown in Table 4, nail cosmetic compositions were prepared in a conventional manner and the quality of the respective compositions was evaluated.

TABLE 4

|  | Example 8 | Example 9 |
|---|---|---|
| Nitrocellulose | 15.0 | 15.0 |
| Alkyd resin | 5.0 | 5.0 |
| Acrylic resin | 5.0 | 5.0 |
| Acetyltriethyl citrate | 5.0 | 5.0 |
| Organic bentonite (Benton 38) | 0.2 | 3.0 |
| Isopropyl alcohol | 3.0 | 3.0 |
| Ethyl acetate | 15.0 | 15.0 |
| n-Butyl acetate | 44.8 | 43.9 |
| Butyl alcohol | 3.0 | 3.0 |
| Pigment (Red color 202 1 Titanium dioxide 1) | 1.0 | 1.0 |
| Pearl agent | 1.0 | 1.0 |
| Silica | 2.0 | 0.1 |
| particle size (μ) | (0.012) | (0.007) |
| Sodium myristic sulfate | 0.1 | 1.5 |
| Viscosity (cps) | 700 | 2000 |
| Stability with elapse of time | ◉ | ◉ |
| Gloss of coating | ◉ | ◉ |
| Durability (peeling) with elapse of time | ◉ | ◉ |
| Safety when used on | ○ | ○ |

TABLE 4-continued

| | Example | |
|---|---|---|
| | 8 | 9 |
| human body | | |

As apparent from the results shown in Table 4, Examples 8 and 9 are safe for use on the human body and have excellent stability with the elapse of time without sedimentation of the pigment or pearl agent contained therein, and have excellent physical properties such as coating and useability.

We claim:

1. A nail cosmetic composition comprising 0.2 to 3.0% by weight of an organically modified montmorillonite, 0.1 to 2.0% by weight of a silica having a particle size of less than 0.01 μm, 60 to 85% by weight of a nonaromatic solvent, a film former and a plasticizer.

2. A nail cosmetic composition as claimed in claim 1, wherein the content of the organically modified montmorillonite is 0.8 to 2.0% by weight.

3. A nail cosmetic composition as claimed in claim 1, wherein the content of the silica is 0.5 to 1.5% by weight.

4. A nail cosmetic composition comprising 0.2 to 3.0% by weight of an organically modified montmorillonite, 0.1 to 2.0% by weight of a silica having a particle size of less than 0.01 μm, 0.01 to 1.5% by weight of an anionic surfactant, 60 to 85% by weight of a nonaromatic solvent, a film former and a plasticizer.

5. A nail cosmetic composition as claimed in claim 4, wherein the content of the organically modified montmorillonite is 0.8 to 2.0% by weight.

6. A nail cosmetic composition as claimed in claim 4, wherein the content of the silica is 0.5 to 1.5% by weight.

7. A nail cosmetic composition as claimed in claim 4, wherein the content of the anionic surfactant is 0.1 to 1.0% by weight.

8. A nail cosmetic composition as claimed in claim 4, wherein the anionic surfactant is at least one surfactant selected from the group consisting of sulfosuccinates, N-acylsacosinates, alkyl sulfate salts, and polyoxyethylene alkyl ether sulfate salts.

* * * * *